United States Patent [19]
Dauth et al.

[11] Patent Number: 5,627,296
[45] Date of Patent: May 6, 1997

[54] PHOSPHORUS-CONTAINING ORGANOSILICON COMPOUNDS

[75] Inventors: Jochen Dauth; Hans Mayer; Bernward Deubzer, all of Burghausen; Petra Gratzl, Túsling, all of Germany

[73] Assignee: Wacker-Chemie GmbH, Munich, Germany

[21] Appl. No.: 559,269

[22] Filed: Nov. 15, 1995

[30] Foreign Application Priority Data

Jan. 5, 1995 [DE] Germany ............ 195 00 253.9

[51] Int. Cl.$^6$ ............................................ C07F 7/08
[52] U.S. Cl. ............................................ 556/405; 556/404
[58] Field of Search ............................................ 556/404, 405

[56] References Cited

U.S. PATENT DOCUMENTS

| | | |
|---|---|---|
| 2,889,349 | 6/1959 | Garden et al. . |
| 2,963,503 | 12/1960 | Marsden . |
| 3,122,581 | 2/1964 | Pike . |
| 3,912,774 | 10/1975 | Kotzsch et al. . |
| 4,292,434 | 9/1981 | Lindner et al. . |
| 4,772,408 | 9/1988 | Mohr et al. ............ 556/405 X |
| 4,948,918 | 8/1990 | Kleiner et al. ............ 556/405 |
| 4,970,138 | 11/1990 | Lauke et al. ............ 556/405 X |

FOREIGN PATENT DOCUMENTS

| | | |
|---|---|---|
| 0110370 | 4/1987 | European Pat. Off. . |
| 2219983 | 1/1975 | Germany . |
| 836241 | 6/1960 | United Kingdom . |
| 885466 | 12/1961 | United Kingdom . |

OTHER PUBLICATIONS

English Derwent abstract AN 73–70808U (1995).
Journal of organic chemistry, vol. 25, No. 7 –1960, pp. 1191–1194 Garrett Barnes "Synthesis and hydrolytic stability of some organosilicon . . . ".
Journal of Polymer Science, Polymer Chemistry Edition, vol. 25, No. 7, 1987, pp. 1967–1978.

*Primary Examiner*—Paul F. Shaver
*Attorney, Agent, or Firm*—Martin Connaughton

[57] ABSTRACT

The present invention provides novel phosphorus-containing organosilicon compounds which can be prepared in a simple manner using readily obtainable starting materials, which are hydrophilic to water-soluble and whose hydrophilicity or water-solubility can be specifically controlled by modification of the phosphorus-containing organosilicon compounds.

4 Claims, No Drawings

PHOSPHORUS-CONTAINING ORGANOSILICON COMPOUNDS

BACKGROUND OF INVENTION

Phosphorus-containing silanes and organo(poly)siloxanes with pentavalent phosphorus are already known. A number of phosphorus-containing silanes and organo(poly)siloxanes, based on phosphonic or phosphinic acid esters are described in U.S. Pat. No. 2,963,503 and U.S. Pat. No. 3,122,581. The radical-initiated hydrophosphorylation reaction gives organosilicon compounds containing phosphonic acid ester radicals and phosphinic acid ester radicals.

GB-A 885 466, DE-B 22 19 983 and U.S. Pat. No. 3,912,774 describe various processes for the preparation of phosphorus-containing silanes and organo(poly)siloxanes.

SUMMARY OF INVENTION

The object of the present invention was to provide phosphorus-containing organosilicon compounds which can be prepared in a simple process using readily obtainable starting materials, which are hydrophilic to water-soluble and whose hydrophilicity or water-solubility can be specifically controlled by modification of the phosphorus-containing organosilicon compounds.

The present invention provides phosphorus-containing organosilicon compounds with units of the formula

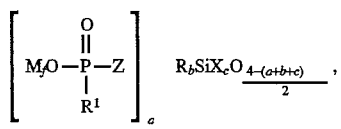   (I)

wherein

R is identical or different and is a monovalent, optionally halogenated hydrocarbon radical having 1 to 18 carbon atoms per radical, $R^1$ is a hydrogen atom, a hydroxyl group, a monovalent hydrocarbon radical having 1 to 18 carbon atoms per radical, or a radical of the formula

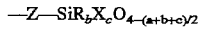

wherein

Z is a divalent hydrocarbon radical having 2 to 18 carbon atoms per radical,

M is an alkali metal or alkaline earth metal,

X is identical or different and is a halogen atom or a radical of the formula $-OR^2$, $R^2$ is an alkyl radical having 1 to 8 carbon atoms per radical, optionally substituted by an ether oxygen atom, a is 0, 1, 2, 3 or 4, b is 0, 1, 2 or 3, c is 0, 1, 2 or 3, the sum of $a+b+c \geq 4$ and f is 0.5 or 1.

The present invention provides a process for the preparation of phosphorus-containing organosilicon compounds, wherein organosilicon compounds (1) having aliphatic multiple bonds and having units of the formula

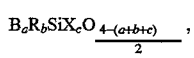   (II)

wherein

B is a monovalent hydrocarbon radical having aliphatic multiple bonds and having 2 to 18 carbon atoms per radical, and R, X, a, b and c are as defined above, are reacted with alkali metal or alkaline earth metal salts of the phosphinic or phosphonic acid (2), of the formula

   (III)

wherein $R^3$ is a hydrogen atom, a hydroxyl group or a monovalent hydrocarbon radical having 1 to 18 carbon atoms per radical, and M is an alkali metal or alkaline earth metal, in the presence of catalysts (3) which form free radicals.

The organosilicon compounds according to the invention preferably have a molecular weight $M_n$ of 100 to 1,000,000 g/mole, more preferably 300 to 90,000 g/mole, and are preferably solids or have a viscosity of 100 to 100,000 $mm^2 \cdot s^{-1}$ at 25° C., preferably 1,000 to 5,000 $mm^2 \cdot s^{-1}$ at 25° C.

Examples of the radical R are alkyl radicals, such as the methyl, ethyl, n-propyl, iso-propyl, 1-n-butyl, 2-n-butyl, isobutyl, tert-butyl, n-pentyl, iso-pentyl, neo-pentyl and tert-pentyl radicals, hexyl radicals, such as the n-hexyl radical, heptyl radicals, such as the n-heptyl radical, octyl radicals, such as the n-octyl radical and iso-octyl radicals, such as the 2,2,4-trimethylpentyl radical, nonyl radicals, such as the n-nonyl radical, decyl radicals, such as the n-decyl radical, dodecyl radicals, such as the n-dodecyl radical; and octadecyl radicals, such as the n-octadecyl radical; cycloalkyl radicals such as the cyclopentyl, cyclohexyl and cycloheptyl radicals and methylcyclohexyl radicals; aryl radicals such as the phenyl, naphthyl, anthryl and phenanthryl radicals; alkaryl radicals such as o-, m- and p-tolyl radicals, xylyl radicals and ethylphenyl radicals; and aralkyl radicals such as the benzyl radical and the α- and β-phenylethyl radicals. The methyl radical is preferred.

Examples of halogenated radicals R are halogenoalkyl radicals such as the 3,3,3-trifluoro-n-propyl radical, the 2,2,2,2',2',2'-hexafluoroisopropyl radical and the heptafluoroisopropyl radical, and halogenoaryl radicals such as the o-, m- and p-chlorophenyl radicals.

Examples of hydrocarbon radicals R apply in their entirety to hydrocarbon radicals $R^1$. Preferably, $R^1$ is a hydrogen atom, a hydroxyl group or a radical of the formula

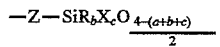

wherein Z, X, R, a, b and c are as defined above.

Examples of divalent hydrocarbon radicals Z are linear and branched alkylene radicals such as radicals of the formulae $-CH_2CH_2-$, $-CH_2CH_2CH_2-$,

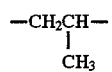

and $-(CH_2)_6-$, and cycloalkylene radicals such as the radical of the formula $-C_6H_{10}-$. The radical of the formula $-CH_2CH_2-$ is preferred.

Examples of alkali metals or alkaline earth metals M are lithium, sodium, potassium, rubidium, cesium, magnesium, calcium, strontium and barium. Alkali metals are preferred, therefore f is preferably 1. Sodium and potassium are more preferred.

Examples of halogen atoms X are the chlorine and bromine atoms.

Examples of alkyl radicals $R^2$ are methyl, ethyl, n-propyl, isopropyl, 1-n-butyl, 2-n-butyl, isobutyl and tert-butyl radicals. The methyl and ethyl radicals are preferred. Examples of alkyl radicals $R^2$ substituted by an ether oxygen atom are the methoxyethyl and ethoxyethyl radicals.

Examples of hydrocarbon radicals B having aliphatic multiple bonds in formula (II) are alkenyl radicals such as the vinyl, allyl, but-1-enyl, pent-1-enyl, hex-1-enyl, divinylcyclohexyl, norbornenyl and cycloheptadienyl radicals. The vinyl radical is preferred.

Examples of hydrocarbon radicals $R^1$ apply in their entirety to hydrocarbon radicals $R^3$. $R^3$ is preferably a hydrogen atom or a hydroxyl group.

The phosphorus-containing organosilicon compounds according to the invention are preferably phosphorus-containing silanes or phosphorus-containing organo(poly)siloxanes.

In formulae (I) and (II), a is preferably 0.01 to 2.0 on average, b is preferably 0.0 to 3.0 on average, c is preferably 0.0 to 3.0 on average and the sum a+b+c is preferably 0.1 to 4.0 on average.

Examples of phosphorus-containing organosilicon compounds are those containing units of the formulae

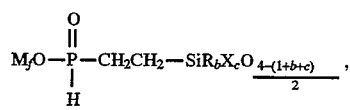     (IV)

or

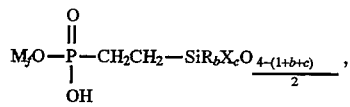     (V)

or

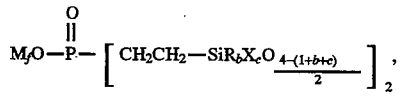     (VI)

wherein M, R, X, b, f and c are as defined above, M is preferably sodium, R is preferably a methyl radical, b is preferably 2, c is preferably 0 and f is preferably 1.

Examples of organosilicon compounds (1) having aliphatic multiple bonds are organo(poly)siloxanes made up of units of the formulae $R_2SiO$ and $BR_2SiO_{1/2}$, $R_3SiO_{1/2}$ and $BRSiO$; $R_3SiO_{1/2}$, $R_2SiO$ and $BRSiO$; $SiO_2$ and $BR_2SiO_{1/2}$; $SiO_2$, $R_2SiO$ and $BR_2SiO_{1/2}$; $RSiO_{3/2}$, $R_2SiO$ and $BR_2SiO_{1/2}$, $RSiO_{3/2}$, $BRSiO$ and $R_3SiO_{1/2}$; $BSiO_{3/2}$ and $R_3SiO_{1/2}$, wherein R and B are as defined above.

Examples of salts (2) used in the process according to the invention are those of the formulae

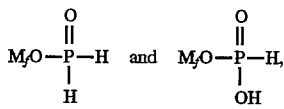

wherein M is defined as indicated above and is preferably sodium or potassium, more preferably sodium.

In the process according to the invention, 0.1–10 mole, preferably 0.5–5 mole and more preferably 0.5–2 mole of Si-bonded groups having aliphatic multiple bonds in the organosilicon compound (1) are used per mole of P-bonded hydrogen in the salt (2).

Peroxide compounds and azo compounds are preferably used as radical-forming catalysts (3) in the process according to the invention.

Examples of peroxide compounds are ditertiary butyl peroxide, dibenzoyl peroxide, diacetyl peroxide, dicumyl peroxide, tertiary butyl peracetate and tertiary butyl perbenzoate. Examples of azo compounds are azoisobutyronitrile, 4,4'-azobis(4-cyanopentanoic acid), 2,2'-azobis(2-cyanopropanol) and phenylazoethane-1,1-dinitrile.

In the process according to the invention, radical-forming catalysts (3) are preferably used in amounts of 0.1% to 10% by weight, preferably in amounts of 2% to 8% by weight, based on the total weight of organosilicon compound (1) and salt (2).

The process according to the invention for the preparation of phosphorus-containing organosilicon compounds is preferably carried out in the presence of organic solvents such as methanol, ethanol, isopropanol, n-butanol, acetone, tetrahydrofuran, dimethylformamide, dimethyl sulfoxide, N-methylpyrrolidone, ethyl acetate and dimethoxyethane, or in the presence of a mixture of water and the organic solvent.

The process according to the invention is preferably carried out at ambient atmospheric pressure, i.e., at about 1020 hPa (abs.), but it can also be carried out at higher or lower pressures. Furthermore, the process according to the invention is preferably carried out at a temperature of 50° C. to 150° C., preferably 80° C. to 110° C.

Any inert organic solvent or water used is preferably removed by distillation from the phosphorus-containing organosilicon compounds prepared by the process according to the invention.

The process can be carried out batchwise, semicontinuously or fully continuously.

The phosphorus-containing organosilicon compounds obtained by the process according to the invention can be reacted with acids (4) which have a lower pH than the phosphinic or phosphonic acid, according to the following equation:

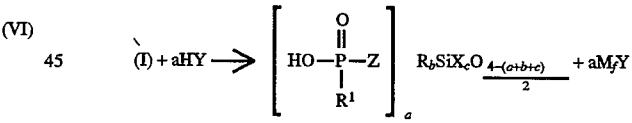

wherein R, $R^1$, X, Z, M, a, b, f and c are as defined above.

Examples of acids HY are those of the formulae $H_2SO_4$, HCl, $HClO_4$, $CF_3COOH$, $H_3PO_4$ and $CF_3SO_3H$.

The low-molecular phosphorus-containing organosilicon compounds according to the invention are mostly solids and readily soluble in water. The addition of acids which have a lower pH than the phosphinic or phosphonic acid precipitates the phosphorus-containing organosilicon compound with the radical $HOP(O)R^1Z$, which can be obtained pure in a simple manner.

The higher-molecular phosphorus-containing organosilicon compounds according to the invention are mostly liquids and mostly self-emulsifying, i.e., the addition of water and rapid stirring produces an emulsion, obviating the need to use an emulsifier. This emulsion is broken by the addition of an acid which has a lower pH than the phosphinic or phosphonic acid, so the phosphorus-containing organosilicon compound with the radical $HOP(O)R^1Z$ can be obtained in a simple manner.

Through this simple modification of the phosphorus-containing organosilicon compound according to the invention, the hydrophilicity or water-solubility can be specifically varied as required. This property is advantageous when applied in the field of textiles.

Furthermore, the phosphorus-containing organosilicon compounds according to the invention which have excess Si-bonded groups B, i.e., groups with an aliphatic multiple bond, can be reacted in a hydrosilylation reaction with organosilicon compounds (5) having at least one Si-bonded hydrogen atom per molecule, of the formula $$H_d R_e SiO_{\frac{4-(d+e)}{2}},\qquad (VII)$$

wherein R is defined as indicated above, d is 0 or 1 and on average 0.01 to 1.0, e is 0, 1, 2 or 3 and on average 0.0 to 3.0 and the sum d+e is not greater than 3, in the presence of hydrosilylation catalysts, i.e., catalysts (6) which promote the addition of Si-bonded hydrogen onto an aliphatic multiple bond.

The organosilicon compounds (5) with at least one Si-bonded hydrogen atom per molecule preferably contain at least 0.04% by weight, preferably 0.1% to 1.6% by weight, of Si-bonded hydrogen and their average viscosity is 5 to 20,000 mm$^2 \cdot$s$^{-1}$ at 25° C., preferably 10 to 10,000 mm$^2 \cdot$s$^{-1}$ at 25° C. and more preferably 10 to 1,000 mm$^2 \cdot$s$^{-1}$ at 25° C.

Preferred organosilicon compounds (5) with at least one Si-bonded hydrogen atom per molecule are organopolysiloxanes of the formula $$H_h R_{3-h} SiO(SiR_2 O)_o (SiRHO)_p SiR_{3-h} H_h \qquad (VIII)$$

wherein R is defined as above, h is 0 or 1, o is 0 or an integer from 1 to 1500 and p is 0 or an integer from 1 to 100.

In the process according to the invention, catalysts (6) which promote the addition of Si-bonded hydrogen onto an aliphatic multiple bond can also be the same catalysts as those which could be used for promoting the addition of Si-bonded hydrogen onto an aliphatic multiple bond. The catalysts are preferably a metal from the platinum metal group or a compound or complex from the platinum metal group. Examples of such catalysts are freely divided platinum metal, which can be present on supports such as silicon dioxide, aluminum oxide or active carbon, compounds or complexes of platinum, such as platinum halides, e.g., PtCl$_4$, H$_2$PtCl$_6$*6H$_2$O or Na$_2$PtCl$_4$*4H$_2$O, platinum/olefin complexes, platinum/alcohol complexes, platinum/alcoholate complexes, platinum/ester complexes, platinum/aldehyde complexes, platinum/ketone complexes, including reaction products of H$_2$PtCl$_6$*6H$_2$O and cyclohexanone, platinum/vinylsiloxane complexes such as platinum/1,3-divinyl-1,1,3,3-tetramethyldisiloxane complexes, which may or may not contain detectable inorganically bonded halogen, bis(gamma-picoline)platinum dichloride, trimethylenedipyridineplatinum dichloride, dicyclopentadieneplatinum chloride, (dimethyl sulfoxide) -ethyleneplatinum(II) dichloride, cyclooctadieneplatinum dichloride, norbornadieneplatinum dichloride, gammapicolineplatinum dichloride, cyclopentadieneplatinum dichloride and reaction products of platinum tetrachloride with an olefin and a primary amine or secondary amine, or a primary and secondary amine, according to U.S. Pat. No. 4,292,434, such as the reaction product of a solution of platinum tetrachloride in oct-1-ene with sec-butylamine, or ammonium/platinum complexes according to EP-B 110 370.

The catalyst (6) is preferably used in amounts of 2 to 200 ppm by weight (parts by weight per million parts by weight), preferably in amounts of 5 to 50 ppm by weight, calculated as elemental platinum and based on the total weight of phosphorus-containing organosilicon compound and organosilicon compound with at least one Si-bonded hydrogen atom per molecule.

The hydrosilylation reaction is preferably carried out at ambient atmospheric pressure, i.e., at about 1020 hPa (abs.), however it can also be carried out at higher or lower pressures. Furthermore, the hydrosilylation reaction is preferably carried out at a temperature of 80° C. to 150° C., more preferably 110° C. to 125° C.

Inert organic solvents can be used in the hydrosilylation reaction although the use of inert organic solvents is not preferred. Examples of inert organic solvents are toluene, isopropanol, xylene, isophorone, octane isomers and butyl acetate. Any inert organic solvent used is removed by distillation after the hydrosilylation reaction.

Furthermore, the phosphorus-containing organosilicon compounds obtained by the process according to the invention can be equilibrated with organopolysiloxanes (7) selected from the group comprising linear organo polysiloxanes having terminal triorganosiloxy groups, linear organopolysiloxanes having terminal hydroxyl groups, cyclic organopolysiloxanes and copolymers of diorganosiloxane and monoorganosiloxane units.

Linear organopolysiloxanes having terminal triorganosiloxy groups are preferably those of the formula $$R_3 SiO(SiR_2 O)_r SiR_3$$

wherein R is as defined above and r is 0 or an integer with a value of 1 to 1500, linear organopolysiloxanes having terminal hydroxyl groups are preferably those of the formula $$HO(SiR_2 O)_s H$$

wherein R is as defined above and s is an integer with a value of 1 to 1500, cyclic organopolysiloxanes are preferably those of the formula $$(R_2 SiO)_t$$

wherein R is as defined above and t is an integer from 3 to 12, and copolymers are preferably those made up of units of the formulae $$R_2 SiO$$

and $$RSiO_{3/2},$$

wherein R is defined as indicated above.

The proportions of the organopolysiloxanes and organopolysiloxanes having phosphorus groups, used in the optional equilibration reaction, are determined only by the desired proportion of phosphorus groups in the organopolysiloxanes produced in the optional equilibration reaction, and by the desired average chain length.

The optional equilibration reaction is preferably carried out using basic catalysts which promote the equilibration. Examples of such catalysts are alkali metal hydroxides, especially potassium and cesium hydroxides, alkali metal alcoholates, quaternary ammonium hydroxides such as tetramethylammonium hydroxide, tetrabutylammonium hydroxide, benzyltrimethylammonium hydroxide, benzyltriethylammonium hydroxide, benzyltrimethylammonium butylate and β-hydroxyethyltrimethylammonium 2-ethylhexanoate, quaternary phosphonium hydroxides such as tetra-n-butylphosphonium hydroxide and tri-n-butyl-3-[tris(trimethylsiloxy)silyl]-n-propyl-phosphonium hydroxide, alkali metal siloxanolates, and ammonium organosiloxanolates such as benzyltrimethylammonium ethylsiloxanolate.

Basic catalysts are preferably used in amounts of 200 to 5,000 ppm by weight, more preferably 500 to 1,500 ppm by weight, based on the total weight of the organosilicon compounds used. Although possible, the use of acid equilibration catalysts is not preferred. For the equilibration of the corresponding free acid derivatives, i.e., the phosphorus-containing organopolysiloxanes with the radical HOP(O)R$^1$Z, acid catalysts are preferred.

Examples of acid catalysts are sulfuric acid, phosphoric acid, trifluoromethanesulfonic acid, phosphorus nitridochlorides and acid catalysts which are solid under the reaction conditions, such as acid-activated bleaching earth, acid zeolites, sulfonated carbon and sulfonated styrene/divinylbenzene copolymer.

The optional equilibration reaction is preferably carried out at 80° C. to 150° C. and at ambient atmospheric pressure, i.e., at about 1020 hPa (abs.). If desired, however, higher or lower pressures can also be applied.

The equilibration is preferably carried out in 5% to 20% by weight of a water-miscible or water-immiscible solvent, such as isopropanol or toluene, based on the total weight of the particular organosilicon compounds used. The catalyst can be rendered inactive prior to working-up of the mixture obtained in the equilibration.

The phosphorus-containing organosilicon compounds according to the invention are particularly suitable for use as hydrophilicity modifiers, flameproofing agents, antistatic agents and bactericides and for introducing polar groups into and onto substrates.

EXAMPLE 1

18.64 g (0.1 mole) of divinyltetramethyldisiloxane and 7.5 g (0.163 mole) of ethanol are heated under reflux to 85° C. under a nitrogen atmosphere. A solution of 10.6 g (0.1 mole) of sodium hypophosphite, 6.0 g (0.33 mole) of water and 1.0 g (0.0031 mole) of 4,4'-azobis(4-cyanopentanoic acid) (10% by weight in water, neutralized to pH 7 with sodium hydroxide) is slowly added dropwise, with stirring. The mixture is then stirred for one hour at 85° C. The solution is filtered and concentrated under high vacuum at 70° C. The concentrate is dried to constant weight under high vacuum at 100° C. over phosphorus pentoxide to give 9.79 g (33.48% of theory) of a white solid. The polymer obtained is made up of units of the formula

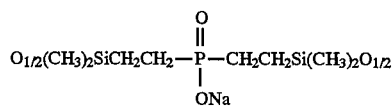

EXAMPLE 2

186.4 g (1 mole) of divinyltetramethyldisiloxane and 75 g (1.63 mole) of ethanol are heated under reflux to 85° C. under a nitrogen atmosphere. A solution of 17.67 g (0.167 mole) of sodium hypophosphite, 10 g (0.56 mole) of water and 16 g (0.049 mole) of 4,4'-azobis(4-cyanopentanoic acid) (10% by weight in water, neutralized to pH 7 with sodium hydroxide) is slowly added dropwise, with stirring. The mixture is then stirred for three hours at 80° C. The solution is filtered and concentrated under high vacuum at 100° C. The concentrate is dried to constant weight under high vacuum at 100° C. over phosphorus pentoxide to give 43.92 g (54.96% of theory) of a white solid which is readily soluble in water. The compound obtained has the formula

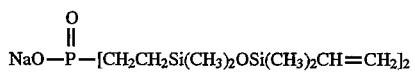

EXAMPLE 3

18.64 g (0.1 mole) of divinyltetramethyldisiloxane and 7.5 g (0.163 mole) of ethanol are heated under reflux to 85° C. under a nitrogen atmosphere. A solution of 21.2 g (0.2 mole) of sodium hypophosphite, 5.0 g (0.28 mole) of water and 1.0 g (0.0031 mole) of 4,4'-azobis(4-cyanopentanoic acid) (10% by weight in water, neutralized to pH 7 with sodium hydroxide) is slowly added dropwise, with stirring. The mixture is then stirred for one hour at 85° C. The solution is filtered and concentrated under high vacuum at 70° C. The concentrate is dried to constant weight under high vacuum at 100° C. over phosphorus pentoxide to give 14.76 g (37.05% of theory) of a white solid. The compound obtained has the formula

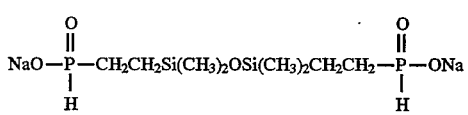

EXAMPLE 4

200 g (11.11 mole) of water and 150 g of 10% by weight aqueous hydrochloric acid are added to 12.86 g of the product of Example 2 and the mixture is stirred for a half hour at room temperature. 50 ml of diethyl ether are added three times to the aqueous emulsion and, after thorough mixing, the organic phase is separated off. The combined diethyl ether phases are dried over sodium sulfate, filtered and concentrated to constant weight under vacuum at 40° C. to give 7.65 g (74.36% of theory) of a clear colorless liquid. The compound obtained has the formula

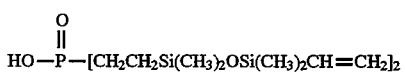

EXAMPLE 5

80 ml (0.99 mole) of tetrahydrofuran and 28.85 μl of a platinum catalyst in oct-1-ene (5.63% by weight of platinum) are added to 9.76 g of the product of Example 2, the total mixture containing 50 ppm by weight of platinum, and the mixture is heated to 65° C. 3.33 g of an α,ω-dihydrogenopolydimethylsiloxane of viscosity 2.4 mm$^2 \cdot$s$^{-1}$, with 0.3% by weight of Si-bonded hydrogen, are then metered in. The solution is stirred for two hours at 65° C. under reflux, an additional 28.85 μl of the above-described platinum catalyst being added after one hour. After filtration, the filtrate is concentrated to constant weight under high vacuum at 80° C. to give 14.34 g (62.07% of theory) of a transparent high-viscosity oil. The polymer obtained is made up of dimethylsiloxane units and units of the formula

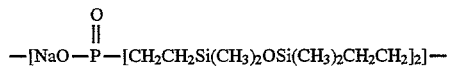

EXAMPLE 6

60 ml (0.66 mole) of n-butanol and 30.63 μl of a platinum catalyst in oct-1-ene (5.63% by weight of platinum) are added to 12.2 g of the product of Example 2, the total mixture containing 50 ppm by weight of platinum, and the mixture is heated to 100° C. 12.32 g (0.075 mole) of hydrogentriethoxysilane are then metered in. The solution is stirred for four hours at 100° C., an additional 30.63 μl of the above-described platinum catalyst being added after two hours. After filtration, the filtrate is concentrated to constant weight under high vacuum at 100° C to give 15.65 g (76.70% of theory) of a transparent viscous oil. The compound obtained has the formula

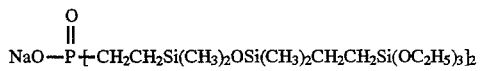

EXAMPLE 7

35.46 g of an α,ω-divinylpolydimethylsiloxane of viscosity 16.7 mm$^2$·s$^{-1}$ at room temperature, with 0.141 mole % of vinyl groups, 15.6 g (0.26 mole) of isopropanol and 0.15 g (9.1×10$^{-4}$ mole) of azoisobutyronitrile are heated to 100° C. under nitrogen. A solution of 2.5 g (2.36×10$^{-2}$ mole) of sodium hypophosphite in 7.0 g (0.15 mole) of ethanol and 4.0 g (0.22 mole) of water is added dropwise. After a reaction time of one hour, an additional 0.15 g (9.1×10$^{-4}$ mole) of azoisobutyronitrile in 15.6 g (0.26 mole) of isopropanol is metered in and the mixture is stirred for a further two hours at 100° C. The solution is filtered and then concentrated to constant weight under high vacuum at 100° C. to give 33.27 g (92.34% of theory) of a colorless high-viscosity product, which forms an emulsion when water is added with rapid stirring, i.e., is self-emulsifying. The polymer obtained is made up of dimethylsiloxane units and units of the formula

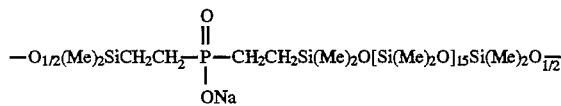

(Me = methyl group)

EXAMPLE 8

25.0 g (1.39 mole) of water, 75.0 g (1.67 mole) of ethanol, 53.0 g (0.5 mole) of sodium hypophosphite and 2.5 g (1.29×10$^{-2}$ mole) of tert-butyl perbenzoate are heated under reflux to 80° C. under nitrogen. 93.0 g (0.5 mole) of 1,3-divinyltetramethyldisiloxane and 2.5 g (1.29×10$^{-2}$ mole) of tert-butyl perbenzoate are mixed and then slowly added dropwise to the above solution. When the addition has ended, the mixture is refluxed for four hours at 85° C. The solution is filtered and concentrated to constant weight under high vacuum at 80° C. to give 138.93 g (95.16% of theory) of a white solid. The polymer obtained is made up of units of the formula

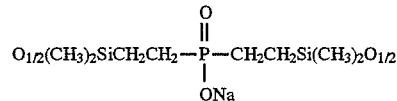

EXAMPLE 9

15 g of silicone resin of viscosity 1460 mm$^2$·s$^{-1}$ at room temperature, made up of SiO$_2$ units and vinyldimethylsiloxane units and having a vinyl content of 0.33 mole %, and 7.5 g (0.163 mole) of ethanol are heated to 80° C. under a nitrogen atmosphere. A solution of 5.253 g (4.96×10$^{-2}$ mole) of sodium hypophosphite, 2.8 g (0.15 mole) of water, 12.0 g (0.26 mole) of ethanol and 0.35 g (1.24×10$^{-3}$ mole) of 4,4'-azobis(4-cyanopentanoic acid) (10% by weight in water, neutralized to pH 7 with sodium hydroxide) is slowly added dropwise, with stirring. The mixture is then stirred for three hours at 80° C. under reflux. The solution is filtered and concentrated under high vacuum at 70° C. The concentrate is dried to constant weight under high vacuum at 100° C. over phosphorus pentoxide to give 16.74 g (82.7% of theory) of a white crystalline resin. The resin obtained is made up of SiO$_2$ units and units of the formula

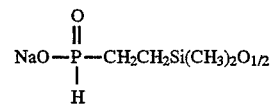

EXAMPLE 10

8.17 g of the product described in Example 6, 34.93 g of an α,ω-dihydroxypolydimethylsiloxane of viscosity 45 mm$^2$·s$^{-1}$, with 0.496 mole % of Si-bonded hydroxyl groups, 26.1 g (0.283 mole) of toluene and 12.9 mg (1.62×10$^{-5}$ mole) of tetrabutylammonium hydroxide * 30 H$_2$O are mixed under a nitrogen atmosphere and stirred for 2 hours under reflux at 120° C. An additional 12.9 mg (1.62×10$^{-5}$ mole) of tetrabutylammonium hydroxide * 30 H$_2$O are then metered in and the mixture is stirred for an additional 2 hours at 120° C. under reflux. The solution is filtered and concentrated to constant weight under high vacuum at 100° C. to give 36.2 g (89.7% of theory) of a translucent oil as an equilibrium mixture.

EXAMPLE 11

5.83 g (0.0313 mole) of divinyltetramethyldisiloxane and 2.34 g (0.051 mole) of ethanol are heated under reflux to 85° C. under a nitrogen atmosphere. A solution of 2.0 g (0.05 mole) of sodium hydroxide, 13.7 g (0.05 mole) of phosphorous acid (30% in water) and 4.3 g (0.0133 mole) of 4,4'-azobis(4-cyanopentanoic acid) (10% by weight in water, neutralized to pH 7 with sodium hydroxide) is slowly added dropwise, with stirring. The mixture is then stirred for three hours at 85° C. under reflux. The solution is filtered and concentrated to constant weight under high vacuum at 100° C. to give 5.93 g (53.8% of theory) of a white solid. The compound obtained has the formula

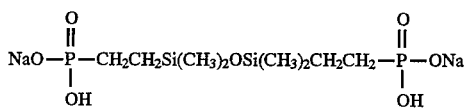

What is claimed is:

1. A process for the preparation of phosphorus-containing organosilicon compounds, of the formula

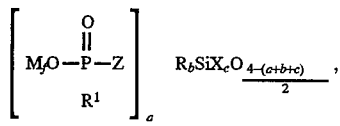

wherein organosilicon compounds having units of the formula

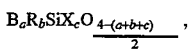

R is identical or different and is a monovalent, optionally halogenated hydrocarbon radical having 1 to 18 carbon atoms per radical, $R^1$ is a hydrogen atom, a hydroxyl group, a monovalent hydrocarbon radical having 1 to 18 carbon atoms per radical, or a radical of the formula

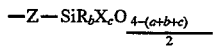

B is a monovalent hydrocarbon radical having aliphatic multiple bonds and having 2 to 18 carbon atoms per radical, Z is a divalent hydrocarbon radical having 2 to 18 carbon atoms per radical, X is identical or different and is a halogen atom or a radical of the formula $-OR^2$, $R^2$ is an alkyl radical having 1 to 8 carbon atoms per radical, optionally substituted by an ether oxygen atom, a is 0, 1, 2, 3 or 4,
b is 0, 1, 2 or 3,
c is 0, 1, 2 or 3,
c is 0, 1, 2 or 3,
the sum a+b+c≧4, are reacted with alkali metal or alkaline earth metal salts of phosphinic or phosphonic acid of the formula

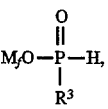 (III)

wherein $R^3$ is a hydrogen atom, a hydroxyl group or a monovalent hydrocarbon radical having 1 to 18 carbon atoms per radical, M is an alkali metal or alkaline earth metal and f is 0.5 or 1, in the presence of catalysts (3) which form free radicals.

2. The process as claimed in claim 1 wherein the phosphorus-containing organosilicon compounds are further reacted with acids which have a lower pH than the phosphinic or phosphonic acid.

3. The process as claimed in claim 1 wherein the phosphorus-containing organosilicon compounds which still contain Si-bonded groups having aliphatic multiple bonds are reacted with organosilicon compounds (5) having at least one Si-bonded hydrogen atom per molecule, in the presence of catalysts (6) which promote the addition of Si-bonded hydrogen onto aliphatic multiple bonds.

4. The process as claimed in claim 1, 2 or 3, wherein the phosphorus-containing organosilicon compounds are equilibrated with organopolysiloxanes (7) selected from the group comprising linear organopolysiloxanes having terminal triorganosiloxy groups, linear organopolysiloxanes having terminal hydroxyl groups, cyclic organopolysiloxanes and copolymers of diorganosiloxane and monoorganosiloxane units.

* * * * *